(12) United States Patent
Murai et al.

(10) Patent No.: US 11,453,648 B2
(45) Date of Patent: Sep. 27, 2022

(54) METHOD FOR PRODUCING OROTIC ACID DERIVATIVE

(71) Applicant: SHOWA DENKO K.K., Tokyo (JP)

(72) Inventors: Motoki Murai, Kawasaki (JP); Akira Shibuya, Kawasaki (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 17/291,662

(22) PCT Filed: Nov. 7, 2019

(86) PCT No.: PCT/JP2019/043677
§ 371 (c)(1),
(2) Date: May 6, 2021

(87) PCT Pub. No.: WO2020/100712
PCT Pub. Date: May 22, 2020

(65) Prior Publication Data
US 2022/0002253 A1    Jan. 6, 2022

(30) Foreign Application Priority Data

Nov. 12, 2018   (JP) .............................. JP2018-212455

(51) Int. Cl.
*C07D 239/557* (2006.01)
*C07D 239/545* (2006.01)

(52) U.S. Cl.
CPC ..... *C07D 239/557* (2013.01); *C07D 239/545* (2013.01)

(58) Field of Classification Search
CPC .................. C07D 239/545; C07D 239/557
See application file for complete search history.

(56) References Cited

U.S. PATENT DOCUMENTS

| | | |
|---|---|---|
| 2005/0176999 A1 | 8/2005 | Yamashita et al. |
| 2009/0156812 A1 | 6/2009 | MacDougall et al. |
| 2019/0224199 A1 | 7/2019 | Yagyu et al. |

FOREIGN PATENT DOCUMENTS

| | | |
|---|---|---|
| EP | 2 495 243 A1 | 9/2012 |
| JP | 43-14708 B1 | 6/1968 |
| JP | 5-310710 A | 11/1993 |
| JP | 2006-115729 A | 5/2006 |
| WO | 03/066563 A1 | 8/2003 |
| WO | 2009/076743 A1 | 6/2009 |
| WO | 2011/115069 A1 | 9/2011 |
| WO | 2018/012157 A1 | 1/2018 |

OTHER PUBLICATIONS

International Search Report for PCT/JP2019/043677 dated Feb. 10, 2020 (PCT/ISA/210).
Herman Gershon, "Pyrimidines II. Chlorinated Pyrimidines Derived from Orotic Acid", The Journal of Organic Chemistry, American Chemical Society, vol. 27, No. 10, Oct. 1962, pp. 3507-3510, XP002585031, ISSN: 0022-3263 (4 pages total).
Extended European Search Report dated May 25, 2022 from the European Patent Office in EP Application No. 19883396.4.

*Primary Examiner* — Deepak R Rao
(74) *Attorney, Agent, or Firm* — Sughrue Mion, PLLC

(57) ABSTRACT

Provided is a method for producing an orotic acid derivative, the method comprising a condensation step of performing, under a basic condition, a condensation reaction between an orotic acid halide represented by General Formula (I) and a compound represented by General Formula (II) to generate an orotic acid derivative represented by General Formula (III); and a neutralization crystallization step of precipitating crystals of orotic acid by neutralization crystallization to separate a liquid containing the orotic acid derivative from the crystals of orotic acid, after the condensation step. In General Formula (I), (II), or (III), X is a halogen atom, and A is a group represented by General Formula (A-1) or (A-2). In General Formula (A-1) or (A-2), $R^1$ is a hydrogen atom or an organic group, and $R^2$ and $R^3$ are each independently an organic group. In a case where $R^1$ is an organic group, $R^1$ and $R^2$ may be bonded to each other to form a ring.

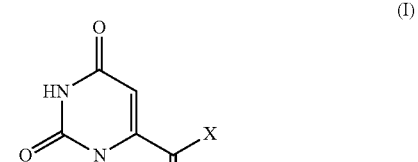

(I)

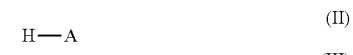

(II)

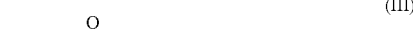

(III)

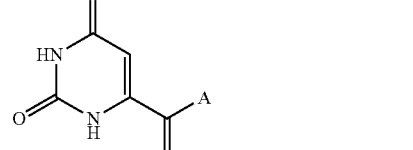

(A-1)

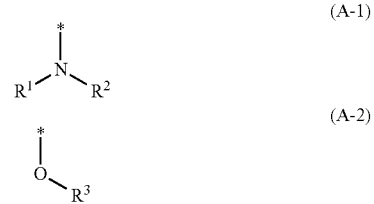

(A-2)

14 Claims, No Drawings

METHOD FOR PRODUCING OROTIC ACID DERIVATIVE

CROSS REFERENCE TO RELATED APPLICATIONS

This application is a National Stage of International Application No. PCT/JP2019/043677 filed Nov. 7, 2019, claiming priority based on Japanese Patent Application No. 2018-212455 filed Nov. 12, 2018.

TECHNICAL FIELD

The present invention relates to a method for producing an orotic acid derivative.

Priority is claimed on Japanese Patent Application No. 2018-212455, filed Nov. 12, 2018, the content of which is incorporated herein by reference.

BACKGROUND ART

Orotic acid is known to have various actions effective for maintaining and promoting health, such as a uric acid level-lowering action, an anti-inflammatory action, a nutritive analeptic action, and a liver function-promoting action. However, it is extremely difficult to dissolve orotic acid in water or alcohol, and thus it is difficult to blend orotic acid in a pharmaceutical drug, a cosmetic, a food, or the like. As a result, attempts have been made to use an orotic acid derivative having improved solubility in water while maintaining the physiological activity of orotic acid.

As a method for activating the carboxy group of orotic acid to synthesize an orotic acid derivative, an acid chloride method, an acid anhydride method, and an active ester method are known. However, since orotic acid has very low solubility in an organic solvent used industrially, problems such as a decrease in the reaction rate caused by carrying out the reaction at a low concentration easily occur. In addition, purification by column chromatography or the like may be required to remove by-products. As a result, it is difficult to industrially produce an orotic acid derivative.

Patent Document 1 discloses a method for producing an orotic acid derivative by an active esterification method. However, in the method described in Patent Document 1, the cost of the reagent itself is high, and column chromatography is performed for purification. Further, dichloromethane (DCM), which is a halogenic solvent, is used as the reaction solvent. Therefore, it is not suitable for industrial implementation.

CITATION LIST

Patent Document

[Patent Document 1]
PCT International Publication No. WO2009/076743

SUMMARY OF INVENTION

Technical Problem

As described above, the conventional method for producing an orotic acid derivative is not a suitable method for industrial implementation.

An object of the present invention is to provide an inexpensive and industrially feasible method for producing an orotic acid derivative.

Solution to Problem

The present invention includes the following aspects.

[1] A method for producing an orotic acid derivative, including a condensation step of performing, under a basic condition, a condensation reaction between an orotic acid halide represented by General Formula (I) and a compound represented by General Formula (II) to generate an orotic acid derivative represented by General Formula (III) and a neutralization crystallization step of precipitating crystals of orotic acid by neutralization crystallization to separate a liquid containing the orotic acid derivative from the crystals of orotic acid, after the condensation step.

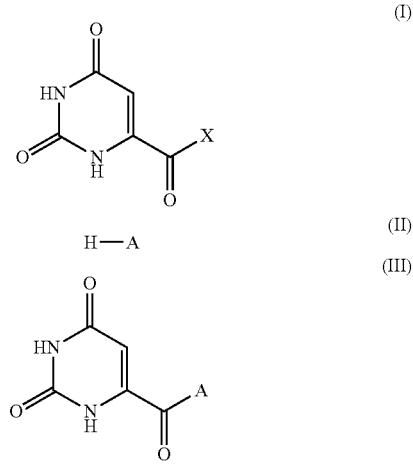

[In the formula, X is a halogen atom, and A is a group represented by General Formula (A-1) or (A-2)]

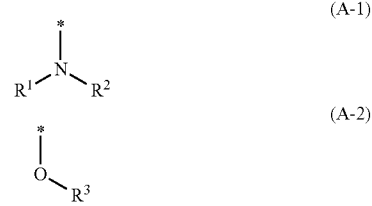

[In the formula, $R^1$ is a hydrogen atom or an organic group, and $R^2$ and $R^3$ are each independently an organic group. In a case where $R^1$ is an organic group, $R^1$ and $R^2$ may be bonded to each other to form a ring. * is a bonding position at which the hydrogen atom in General Formula (II) is bonded.]

[2] The method for producing an orotic acid derivative according to [1], in which in General Formula (A-1), $R^1$ is a hydrogen atom or an organic group having 1 to 10 carbon atoms, and $R^2$ is an organic group having a carboxy group and having 1 to 15 carbon atoms, and in General Formula (A-2), $R^3$ is an organic group having 1 to 15 carbon atoms.

[3] The method for producing an orotic acid derivative according to [1] or [2], in which the compound represented by General Formula (II) is an amino acid.

[4] The method for producing an orotic acid derivative according to [3], in which the amino acid is glutamic acid.

[5] The method for producing an orotic acid derivative according to any one of [1] to [4], in which a solvent used in the condensation step is a non-halogenic solvent.

[6] The method for producing an orotic acid derivative according to [5], in which the solvent is a water-containing solvent.

[7] The method for producing an orotic acid derivative according to [6], in which the solvent is a two-phase solvent of an organic solvent and water.

[8] The method for producing an orotic acid derivative according to [7], in which the organic solvent is tetrahydrofuran or toluene.

[9] The method for producing an orotic acid derivative according to any one of [1] to [8], in which a pH of a liquid phase is set to 4 to 6 in the neutralization crystallization step.

[10] The method for producing an orotic acid derivative according to any one of [1] to [9], further including a secondary neutralization crystallization step of subjecting the liquid containing the orotic acid derivative to neutralization crystallization to precipitate crystals of the orotic acid derivative, after the neutralization crystallization step.

[11] The method for producing an orotic acid derivative according to [10], in which a pH of a liquid phase is set to 0.5 to 2 in the secondary neutralization crystallization step.

[12] The method for producing an orotic acid derivative according to [10] or [11], further including a crystal collection step of collecting the crystals of the orotic acid derivative, after the secondary neutralization crystallization step.

[13] The method for producing an orotic acid derivative according to any one of [1] to [12], further including an orotic acid halogenation step of reacting an orotic acid with a thionyl halide to generate the orotic acid halide, before the condensation step.

[14] The method for producing an orotic acid derivative according to any one of [1] to [13], in which the orotic acid halide is orotic acid chloride.

Advantageous Effects of Invention

The present invention provides an inexpensive and industrially feasible method for producing an orotic acid derivative.

DESCRIPTION OF EMBODIMENTS

In the present specification, a structure is disclosed in which an asymmetric carbon is present and enantiomers or diastereomers may be present, depending on the structure of the chemical formula. In that case, these isomers are represented by one chemical formula. These isomers may be used alone or in the form of a mixture.

In the present specification, a structure is disclosed which may have salt forms, depending on the structure of the chemical formula. In that case, one chemical formula includes the salt forms thereof. Further, in a case where solvate forms may be present, one chemical formula includes the solvate forms thereof.

In the present specification, the term "orotic acid derivative" includes a salt form. Examples of the salt form include an inorganic acid salt, and examples of the inorganic acid salt include a hydrochloride, a sulfate, and a nitrate.

In one embodiment, the present invention provides a method for producing an orotic acid derivative. The production method of the present embodiment includes a condensation step of performing, under a basic condition, a condensation reaction between an orotic acid halide represented by General Formula (I) and a compound represented by General Formula (II) to generate an orotic acid derivative represented by General Formula (III) and a neutralization crystallization step of precipitating crystals of orotic acid by neutralization crystallization to separate a liquid containing the orotic acid derivative from the crystals of orotic acid.

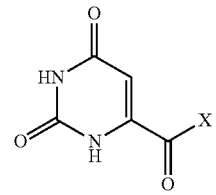

(I)

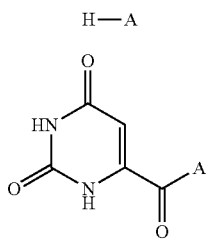

(II)

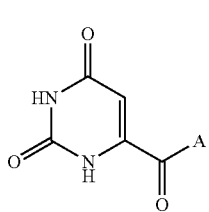

(III)

[In the formula, X is a halogen atom, and A is a group represented by General Formula (A-1) or (A-2)]

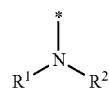

(A-1)

(A-2)

[In the formula, $R^1$ is a hydrogen atom or an organic group, and $R^2$ and $R^3$ are each independently an organic group. In a case where $R^1$ is an organic group, $R^1$ and $R^2$ may be bonded to each other to form a ring. * is a bonding position at which the hydrogen atom in General Formula (II) is bonded.]

[Condensation Step]

The condensation step is a step of performing, under a basic condition, a condensation reaction between an orotic acid halide represented by General Formula (I) and a compound represented by General Formula (II) (hereinafter, may be referred to as a "compound (II)") to generate an orotic acid derivative represented by General Formula (III).

<Orotic Acid Halide: Compound (I)>

The orotic acid halide used in this step is a compound represented by General Formula (I) (hereinafter, also referred to as a "compound (I)"). In General Formula (I), X represents a halogen atom. Examples of the halogen atom include a fluorine atom, a chlorine atom, a bromine atom, and an iodine atom. Among these, a chlorine atom is preferable.

The orotic acid halide can be synthesized by a known method. Examples of the method for synthesizing an orotic acid halide include a method for reacting orotic acid with thionyl halide. Specific examples of the method for synthesizing an orotic acid halide will be described in the section "(Orotic acid halogenation step)" described later.

<Compound (II)>

The compound (II) is a compound represented by General Formula (II). In General Formula (II), A is a group represented by General Formula (A-1) or (A-2). Hereinafter, a compound in which A in General Formula (II) is a group represented by General Formula (A-1) is also described as a "compound (II-1)". A compound in which A in General Formula (II) is a group represented by General Formula (A-2) is also described as a "compound (II-2)".

(Compound (II-1))

The compound (II-1) is a compound in which A in General Formula (II) is represented by General Formula (A-1). In General Formula (A-1), $R^1$ is a hydrogen atom or an organic group. However, among the compounds represented by General Formula (A-1), those corresponding to the compound (I) are excluded.

The organic group as $R^1$ is not particularly limited; however, it preferably has 1 to 10 carbon atoms. Suitable examples of such an organic group include a hydrocarbon group having 1 to 10 carbon atoms, which may have a substituent. The hydrocarbon group may be an aliphatic hydrocarbon group or an aromatic hydrocarbon group.

The aliphatic hydrocarbon group may be a saturated aliphatic hydrocarbon group or an unsaturated aliphatic hydrocarbon group. Examples of the aliphatic hydrocarbon group include a linear or branched aliphatic hydrocarbon group, and an aliphatic hydrocarbon group containing a ring in the structure thereof.

The linear aliphatic hydrocarbon group more preferably has 1 to 5 carbon atoms and still more preferably 1 to 3 carbon atoms. The branched aliphatic hydrocarbon group more preferably has 3 to 10 carbon atoms and still more preferably 3 to 5 carbon atoms.

Specific examples of the linear or branched aliphatic hydrocarbon group include a linear alkyl group such as a methyl group, an ethyl group, an n-propyl group, an n-butyl group, or an n-pentyl group; a branched alkyl group such as an isopropyl group, an isobutyl group, a tert-butyl group, an isopentyl group, a neopentyl group, a 1,1-diethylpropyl group, or a 2,2-dimethylbutyl group; a linear alkenyl group such as a vinyl group, a 2-propenyl group (an allyl group), or a 2-butenyl group; a branched alkenyl group such as a 1-methylvinyl group, a 2-methylvinyl group, a 1-methylpropenyl group, or a 2-methylpropenyl group; a linear alkynyl group such as an ethynyl group, a propargyl group, a 3-pentynyl group; and a branched alkynyl group such as a 1-methylpropargyl group.

The linear or branched aliphatic hydrocarbon group as R may or may not have a substituent. Examples of the substituent include a hydroxy group, a carbonyl group, an alkoxy group, a carboxy group, an amino group, an imino group, and a mercapto group.

The aliphatic hydrocarbon group containing a ring in the structure, as $R^1$, includes an alicyclic hydrocarbon group (a group obtained by removing one hydrogen atom from the aliphatic hydrocarbon ring) and a group obtained by substituting one of the hydrogen atoms of the aliphatic hydrocarbon ring with an alkylene group. The alkylene group preferably has 1 to 4 carbon atoms. The aliphatic hydrocarbon ring preferably has 3 to 10 carbon atoms and more preferably 3 to 6 carbon atoms.

The aliphatic hydrocarbon ring may be a polycyclic ring or a monocyclic ring; however, it is preferably a monocyclic ring.

The monocyclic aliphatic hydrocarbon ring preferably has 3 to 6 carbon atoms. Examples of the monocyclic aliphatic hydrocarbon ring include cyclopropane, cyclobutane, cyclopentane, and cyclohexane.

The polycyclic aliphatic hydrocarbon ring preferably has 7 to 10 carbon atoms. Examples of the polycyclic aliphatic hydrocarbon ring include a polycycloalkane having a cross-linked ring-based polycyclic skeleton. Examples of the polycycloalkane include adamantane, norbornane, and isobornane.

The aliphatic hydrocarbon group containing a ring in the structure, as $R^1$, may or may not have a substituent. Examples of the substituent include a hydroxy group, a carbonyl group, a carboxy group, an amino group, an imino group, a mercapto group, an alkoxy group, an alkyl group, an alkenyl group, and an alkynyl group. The alkyl group as the substituent preferably has 1 to 3 carbon atoms and more preferably 1 or 2 carbon atoms. The alkenyl group or alkynyl group as the substituent preferably has 2 to 4 carbon atoms and more preferably 2 or 3 carbon atoms.

The aromatic hydrocarbon group as $R^1$ may be monocyclic or polycyclic; however, it is preferably monocyclic. The number of carbon atoms in the aromatic ring is preferably 5 to 10 and more preferably 5 to 8.

Examples of the aromatic ring include an aromatic hydrocarbon ring such as a benzene ring or naphthalene ring; and an aromatic heterocycle, in which a part of the carbon atoms constituting an aromatic hydrocarbon ring is substituted with a hetero atom. Examples of the hetero atom in the aromatic heterocycles include an oxygen atom, a sulfur atom, and a nitrogen atom. Examples of the aromatic heterocycle include a pyrrolidine ring, a pyridine ring, and a thiophene ring.

Examples of the aromatic hydrocarbon group as $R^1$ include a group obtained by removing one hydrogen atom from an aromatic hydrocarbon ring or aromatic heterocycle (an aryl group or a heteroaryl group); and a group obtained by substituting one hydrogen atom of an aromatic hydrocarbon ring or aromatic heterocycle with an alkylene group (e.g., an arylalkyl group such as a benzyl group, a phenethyl group, a 1-naphthylmethyl group, a 2-naphthylmethyl group, a 1-naphthylethyl group, or a 2-naphthylethyl group). The number of carbon atoms in the alkylene group bonded to the aromatic hydrocarbon ring or aromatic heterocycle is preferably in a range of 1 to 3, more preferably 1 or 2, and still more preferably 1.

The aromatic hydrocarbon group as $R^1$ may or may not have a substituent. Examples of the substituent include a hydroxy group, a carbonyl group, a carboxy group, an amino group, an imino group, a mercapto group, an alkoxy group, an alkyl group, an alkenyl group, and an alkynyl group. The alkyl group as the substituent preferably has 1 to 3 carbon atoms and more preferably 1 or 2 carbon atoms. The alkenyl group or alkynyl group as the substituent preferably has 2 to 4 carbon atoms and more preferably 2 or 3 carbon atoms.

Among the above, an organic group as $R^1$ is preferably an aliphatic hydrocarbon group, more preferably an alkyl group, and still more preferably an alkyl group having 1 to 5 carbon atoms.

In General Formula (A-1), $R^2$ is an organic group.

The organic group as $R^2$ is not particularly limited; however, it preferably has 1 to 15 carbon atoms. Examples of the organic group as $R^2$ include a hydrocarbon group having 1 to 15 carbon atoms, which may have a substituent. The hydrocarbon group preferably contains at least one carboxy group as a substituent. That is, the organic group as $R^2$ is preferably a hydrocarbon group having 1 to 15 carbon atoms and at least one carboxy group as a substituent. Examples of the hydrocarbon group include the same groups as those exemplified as the organic group as $R^1$.

In a case where $R^1$ is an organic group, $R^1$ and $R^2$ may be bonded to each other to form a ring. The ring structure formed by bonding $R^1$ and $R^2$ to each other is a heterocycle containing a nitrogen atom of General Formula (A-1) in the ring structure. The heterocycle may be an aliphatic heterocycle or an aromatic heterocycle. The ring structure may be monocyclic or polycyclic.

The aliphatic heterocycle as the ring structure formed by $R^1$ and $R^2$ may be a polycyclic ring or a monocyclic ring; however, a monocyclic ring is preferable. The aliphatic heterocycle preferably has 2 to 10 carbon atoms and more preferably 3 to 6 carbon atoms. Examples of the aliphatic heterocycle include an aziridine ring, an azetidine ring, a pyrrolidine ring, a piperidine ring, and a pyrroline ring. The aliphatic heterocycle may contain two or more hetero atoms. Examples of the aliphatic heterocycle containing two or more hetero atoms include a piperazine ring and a morpholine ring.

The aromatic hydrocarbon ring as the ring structure formed by $R^1$ and $R^2$ may be a polycyclic ring or a monocyclic ring; however, a monocyclic ring is preferable. The monocyclic aromatic heterocycle preferably has 2 to 6 carbon atoms. Examples of the monocyclic aromatic heterocycle include an azirine ring, an azete ring, a pyrrole ring, and a pyridine ring. The monocyclic aromatic heterocycle may contain two or more hetero atoms. Examples of the monocyclic aromatic heterocycle containing two or more hetero atoms include an imidazole ring, a pyrazole ring, an oxazole ring, a thiazole ring, an imidazoline ring, a thiazine ring, a triazole ring, a tetrazole ring, a pyrimidine ring, and a pyrazine ring. Examples of the polycyclic aromatic hydrocarbon ring include an indole ring, an isoindole ring, a benzimidazole ring, a quinoline ring, an isoquinoline ring, and a quinazoline ring.

The ring structure formed by $R^1$ and $R^2$ may or may not have a substituent. Examples of the substituent include a hydroxy group, a carbonyl group, a carboxy group, an amino group, an imino group, a mercapto group, an alkoxy group, an alkyl group, an alkenyl group, and an alkynyl group. The alkyl group, alkenyl group, or alkynyl group as the substituent preferably has 1 to 3 carbon atoms and more preferably 1 or 2 carbon atoms.

The ring structure formed by $R^1$ and $R^2$ is preferably an aliphatic heterocycle, more preferably a monocyclic aliphatic heterocycle, still more preferably a pyrrolidine ring or a piperidine ring, and particularly preferably a pyrrolidine ring.

Compound (II-1) can also be represented by General Formula (II-1).

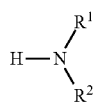

(II-1)

[In the formula, $R^1$ and $R^2$ are the same as those in General Formula (A-1).]

Preferable examples of the compound (II-1) include a compound represented by General Formula (II-1a) (hereinafter, also referred to as a "Compound (II-1a))").

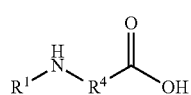

(II-1a)

[In the formula, $R^1$ is a hydrogen atom or an organic group, and $R^4$ is a divalent organic group as a linking group. In a case where $R^1$ is an organic group, $R^1$ and $R^4$ may be bonded to each other to form a ring.]

In General Formula (II-1a), $R^1$ is a hydrogen atom or an organic group. $R^1$ is the same as $R^1$ in General Formula (A-1).

In General Formula (II-1a), $R^4$ is a divalent organic group. The divalent organic group as $R^4$ preferably has 1 to 15 carbon atoms and more preferably 1 to 12 carbon atoms.

Examples of the divalent organic group as $R^4$ include a hydrocarbon group having 1 to 12 carbon atoms, which may have a substituent. The hydrocarbon group may be an aliphatic hydrocarbon group or an aromatic hydrocarbon group; however, it is preferably an aliphatic hydrocarbon group. Preferable examples of the aliphatic hydrocarbon group include an alkylene group. The alkylene group has preferably 1 to 10 carbon atoms, more preferably 1 to 6 carbon atoms, still more preferably 1 to 3 carbon atoms, particularly preferably 1 or 2 carbon atoms, and most preferably one carbon atom.

The hydrocarbon group as $R^4$ may or may not have a substituent. Examples of the substituent include a hydroxy group, a carbonyl group, a carboxy group, an amino group, an imino group, a mercapto group, and an alkoxy group.

In the preferred embodiment, $R^4$ is an alkylene group or a group obtained by substituting one or more hydrogen atoms of the alkylene group with a substituent. Examples of the substituent include a side chain of a natural amino acid or a derivative thereof, in addition to the groups exemplified above. More specific examples of the substituent of the alkylene group as $R^4$ preferably include a side chain of an amino acid selected from the group consisting of alanine, arginine, asparagine, aspartic acid, cysteine, glutamine, glutamic acid, glycine, histidine, isoleucine, leucine, lysine, methionine, phenylalanine, serine, threonine, tryptophan, tyrosine, and valine, and derivatives thereof. Here, "a side chain of a natural amino acid or a derivative thereof" refers to a group represented by R in the α-amino acid represented by General Formula (α).

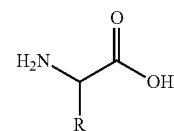

(α)

[In the formula, R represents a side chain of a natural amino acid or a derivative thereof.]

In a case where $R^1$ is an organic group, $R^1$ and $R^4$ may be bonded to each other to form a ring. Examples of the ring structure formed by $R^1$ and $R^4$ being bonded to each other include the same ring structure formed by $R^1$ and $R^2$ in General Formula (A-1).

The ring structure formed by $R^1$ and $R^4$ is preferably an aliphatic heterocycle, more preferably a monocyclic aliphatic heterocycle, still more preferably a pyrrolidine ring or a piperidine ring, and particularly preferably a pyrrolidine ring.

Preferable examples of the compound (II-1a) include a compound represented by General Formula (II-1b) (hereinafter, also referred to as a "Compound (II-1b))").

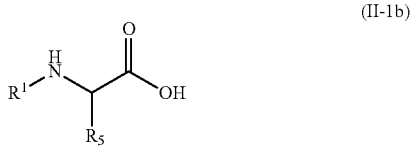

(II-1b)

[In the formula, $R^1$ is a hydrogen atom or an organic group and $R^5$ is a hydrogen atom or an organic group. In a case where $R^1$ is an organic group, $R^1$ and $R^5$ may be bonded to each other to form a ring.

In General Formula (II-1b), $R^1$ is a hydrogen atom or an organic group. $R^1$ is the same as $R^1$ in General Formula (A-1).

In General Formula (II-1b), $R^5$ is a hydrogen atom or an organic group. The organic group as $R^5$ preferably has 1 to 15 carbon atoms, more preferably 1 to 12 carbon atoms, and still more preferably 1 to 10 carbon atoms. Preferable examples of the organic group as $R^5$ include a hydrocarbon group having 1 to 10 carbon atoms, which may have a substituent. Examples of the hydrocarbon group include the same group as the group exemplified as $R^1$ in General Formula (A-1).

Preferable examples of $R^5$ include a side chain of a natural amino acid or a derivative thereof. Among them, $R^5$ is preferably a side chain of an amino acid selected from the group consisting of alanine, arginine, asparagine, aspartic acid, cysteine, glutamine, glutamic acid, glycine, histidine, isoleucine, leucine, lysine, methionine, phenylalanine, serine, threonine, tryptophan, tyrosine, and valine, and derivatives thereof.

In a case where $R^1$ is an organic group, $R^1$ and $R^5$ may be bonded to each other to form a ring. Examples of the ring structure formed by $R^1$ and $R^5$ being bonded to each other include the same ring structure formed by $R^1$ and $R^2$ in General Formula (A-1).

The ring structure formed by $R^1$ and $R^5$ is preferably an aliphatic heterocycle, more preferably a monocyclic aliphatic heterocycle, still more preferably a pyrrolidine ring or a piperidine ring, and particularly preferably a pyrrolidine ring.

In the preferred embodiment, the compound (II-1) is an amino acid or an imino acid and is preferably an amino acid. In the more preferred embodiment, the compound (II-1) is an α-amino acid or an α-imino acid and is more preferably an α-amino acid. Specific examples of the compound (II-1) preferably include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, and derivatives thereof. Among them, the compound (II-1) is preferably glutamic acid, glycine, histidine, or aspartic acid and is more preferably glutamic acid.

The above amino acid may be an L-amino acid, a D-amino acid, or a mixture thereof; however, it is preferably an L-amino acid.

(Compound (II-2))

The compound (II-2) is a compound in which A in General Formula (II) is represented by General Formula (A-2). In General Formula (A-2), $R^3$ is an organic group. However, those corresponding to the compound (I) are excluded.

The organic group as $R^3$ preferably has 1 to 15 carbon atoms, more preferably 1 to 12 carbon atoms, still more preferably 1 to 10 carbon atoms, and particularly preferably 1 to 6 carbon atoms. Examples of the organic group as $R^3$ include a hydrocarbon group having 1 to 15 carbon atoms, which may have a substituent. Examples of the hydrocarbon group include the same group as the group exemplified as $R^1$ in General Formula (A-1).

The hydrocarbon group as $R^3$ may or may not have a substituent. Examples of the substituent include a hydroxy group, a carbonyl group, a carboxy group, a mercapto group, and an alkoxy group.

The organic group as $R^3$ preferably has at least one functional group selected from the group consisting of a hydroxy group and a carboxy group. The organic group as $R^3$ may have any one of a hydroxy group and a carboxy group or may have both of a hydroxy group and a carboxy group.

Preferable examples of the compound (II-2) include hydroxy acids such as lactic acid, citric acid, and hydroxycitric acid; and alkanediols such as ethylene glycol and propylene glycol.

The compound (II-2) can also be represented by General Formula (II-2).

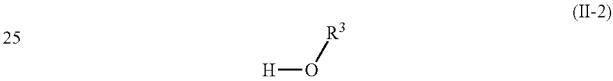

(II-2)

[In the formula, $R^3$ is the same as that in General Formula (A-2).]

The compound (II) may be any one of the compound (II-1) and the compound (II-2); however, it is preferably the compound (II-1).

<Orotic Acid Derivative: Compound (III)>

An orotic acid derivative generated in this step is a compound represented by General Formula (III) (hereinafter, also referred to as a "compound (III)"). In General Formula (III), A is a group represented by General Formula (A-1) or (A-2). Hereinafter, a compound in which A in General Formula (III) is a group represented by General Formula (A-1) is also described as a "compound (III-1)". A compound in which A in General Formula (III) is a group represented by General Formula (A-2) is also described as a "compound (III-2)".

(Compound (III-1))

The compound (III-1) is a compound produced by a condensation reaction between the compound (I) and the compound (II-1).

The compound (III-1) can also be represented by General Formula (III-1). In General Formula (III-1), $R^1$ and $R^2$ are the same as those in General Formula (A-1).

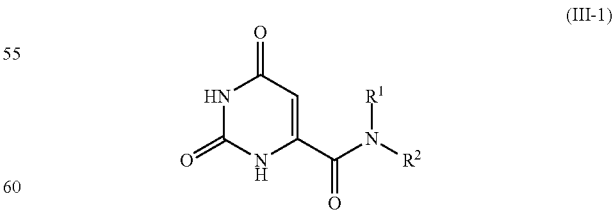

(III-1)

[In the formula, $R^1$ and $R^2$ are the same as those in General Formula (A-1).]

Preferable examples of the compound (III-1) include a compound represented by General Formula (III-1a) (hereinafter, also referred to as a "Compound (III-1a)").

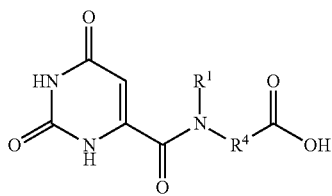

[In the formula, $R^1$ and $R^4$ are the same as those in General Formula (II-1a).]

The compound (III-1a) is a compound generated by a condensation reaction between the compound (I) and the compound (II-1a). In General Formula (III-1a), $R^1$ and $R^4$ are the same as those in General Formula (II-1a).

Preferable examples of the compound (III-1a) include a compound represented by General Formula (III-1b) (hereinafter, also referred to as a "Compound (III-1b)").

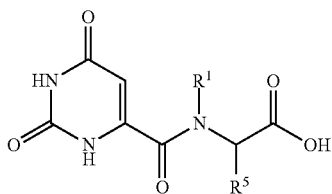

[In the formula, $R^1$ and $R^4$ are the same as those in General Formula (II-1b).]

The compound (III-1b) is a compound generated by a condensation reaction between the compound (I) and the compound (II-1b). In General Formula (III-1b), $R^1$ and $R^5$ are the same as those in General Formula (II-1b).

(Compound (III-2))

The compound (III-2) is a compound generated by a condensation reaction between the compound (I) and the compound (II-2).

The compound (III-2) can be represented by General Formula (III-2). In General Formula (III-2), $R^3$ is the same as that in General Formula (A-2).

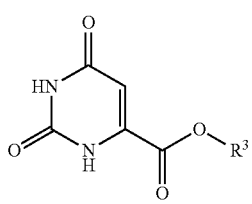

[In the formula, $R^3$ is the same as that in General Formula (A-2).]

<Condensation Reaction>

The condensation reaction between the compound (I) and the compound (II) can be carried out by a known method such as the Schotten-Baumann reaction. The condensation reaction can be carried out, for example, by dissolving the compound (I) and the compound (II) in a suitable solvent, mixing them, and reacting them under a basic condition.

The solvent used in the condensation reaction is not particularly limited; however, from the viewpoint of industrial usability, it is preferably a non-halogenic solvent and more preferably a water-containing solvent. A non-halogenic solvent refers to a solvent containing no halogen atoms. A water-containing solvent refers to a solvent containing water. The water-containing solvent may be a solvent containing water, may be water alone, or may be a two-phase solvent of an organic solvent and water.

The organic solvent used for the two-phase solvent of an organic solvent and water is not particularly limited; however, it is preferably an organic solvent having no functional group (a hydroxy group, an amino group, a mercapto group, or the like) that reacts with an acid halide. Examples of such a solvent include hydrocarbon-based solvents such as toluene, xylene, anisole, hexane, and heptane; and ether-based solvents such as tetrahydrofuran, diethyl ether, and tert-butyl methyl ether.

Among them, from the viewpoint of improving the yield of the compound (III), it is preferable to use a two-phase solvent of an organic solvent and water. The organic solvent is effective in suppressing the decomposition of an acid halide. Since water can easily maintain a specified pH and has a good pH responsiveness, it is easy to secure the solubility of reaction raw materials and target products. For this reason, it is presumed that the two-phase solvent of an organic solvent and water is a system in which the progression of the reaction is promoted and the neutralization (the removal to the outside of system) of the acid generated as a by-product during the reaction easily progresses. As the two-phase solvent of an organic solvent and water, it is more preferable to use a two-phase solvent of toluene and water or a two-phase solvent of tetrahydrofuran and water, and it is still more preferable to use a two-phase solvent of tetrahydrofuran and water. In a case where a two-phase solvent of toluene/water is used, a liquid-liquid separation is easy and operability is excellent.

The mixing ratio of the organic solvent to water in the two-phase solvent of an organic solvent and water is not particularly limited; however, for example, the mixing ratio can be water:organic solvent (mass ratio)=1:0.5 to 1:10. The mixing ratio is preferably water:organic solvent (mass ratio)=1:1 to 1:5, more preferably water:organic solvent (mass ratio)=1:1 to 1:3, and particularly preferably water:organic solvent (mass ratio)=1:2.

As the organic solvent used for the two-phase solvent of an organic solvent and water, only one kind of organic solvent may be used, or two or more kinds thereof may be mixed and used.

In order to make a reaction condition basic, the reaction solution can be made basic by using a base. The base used for making the reaction solution basic is not particularly limited, and an organic base or an inorganic base can be used; however, an inorganic base is preferable. Examples of the organic base include triethylamine and pyridine. Examples of the inorganic base include sodium hydroxide, potassium hydroxide, and calcium hydroxide, and sodium hydroxide is preferable. Further, in order to promote the condensation reaction, a small amount of N,N-dimethyl-4-aminopyridine may be added to the reaction solution.

The reaction temperature in the condensation reaction is preferably 5° C. or lower. The temperature condition during the condensation reaction can be, for example, 0° C. to 5° C.

The pH (the pH of the suspension in a case of using a two-phase solvent) in the condensation reaction may be under a basic condition. The pH during the condensation reaction is preferably maintained at, for example, pH 8 to 13 and is more preferably maintained at pH 10 to 12.

The pressure conditions in the condensation reaction are not particularly limited; however, pressure conditions of normal pressure are preferable.

The reaction time of the condensation reaction is not particularly limited, and it can be appropriately set depending on the amounts of the compound (I) and the compound (II); however, for example, can be set to about 30 to 180 minutes.

During the condensation reaction, it is preferable to stir the reaction solution in order to promote the reaction. The shape of the stirring blade and rotation speed are not particularly limited; however, it is preferable that the crystals present in the reaction solution be homogeneously mixed in the solution.

A glass lining reactor can be used for the condensation reaction. Since a metal container liquates out, the metal container is not suitable as a reaction container for this reaction.

In the reaction solution of the condensation reaction, the concentration of the compound (I) (the orotic acid halide) at the start of the reaction is preferably 1% to 13% by mass and more preferably 1% to 5% by mass. In a case where the concentration of the orotic acid halide is equal to or more than the above lower limit value, the industrial productivity is good, and in a case where the concentration of the orotic acid halide is equal to or less than the above upper limit value, it is possible to prevent a decrease in yield due to the progression of side reactions.

In the reaction solution of the condensation reaction, the concentration ratio (the molar ratio) of the compound (I) (the orotic acid halide) and the compound (II) at the start of the reaction is preferably compound (II)/compound (I)=1 to 3 and is more preferably compound (II)/compound (I)=1 to 2. In a case where the concentration ratio is equal to or more than the above lower limit value, the burden of collecting raw materials can be reduced, and in a case where the concentration ratio is equal to or less than the above upper limit value, the burden of purification can be reduced.

The method for adding the orotic acid halide to the reactor is not particularly limited, and the orotic acid halide may be directly added at one time, or the orotic acid halide may be divided and added in small amounts.

The condensation reaction between the compound (I) and compound (II) is shown below.

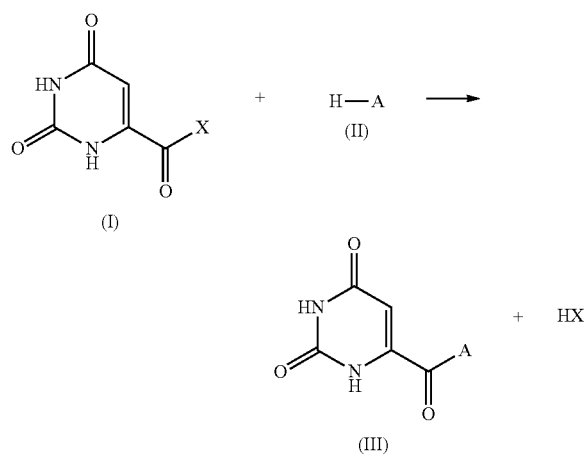

[In the formula, X and A are the same as the above.]

[Neutralization Crystallization Step]

The neutralization crystallization step is a step of precipitating crystals of orotic acid by neutralization crystallization to separate a liquid containing the orotic acid derivative from the crystals of orotic acid. This step is performed after the condensation step.

In the condensation step, the orotic acid halide (the compound (I)) that did not react with compound (II) is hydrolyzed to orotic acid. As a result, orotic acid and the orotic acid derivative (the compound (III)) are mixed in the reaction solution after the condensation step. By this step, orotic acid can be selectively precipitated from the above-described mixed solution of orotic acid and the orotic acid derivative.

The reaction solution after the condensation step can be subjected to neutralization crystallization. Alternatively, in a case where a two-phase solvent of an organic solvent and water is used in the condensation step, the aqueous phase obtained by separating the organic solvent and water after the condensation step may be subjected to neutralization crystallization. Alternatively, the reaction solution may be a liquid containing orotic acid and an orotic acid derivative which has undergone any other treatment after the condensation step.

In a case where a two-phase solvent of an organic solvent and water is used in the condensation step, the method for separating the organic solvent and water after the condensation step is not particularly limited. Examples of the method for separating the organic solvent and water include separation by distilling off the organic solvent and the liquid-liquid separation. In a case where the organic solvent and water are homogeneously mixed, the organic solvent and water can be separated by distilling off the organic solvent, and in a case where the organic solvent and water are phase-separated, the organic solvent and water can be separated by liquid-liquid separation. In a case where tetrahydrofuran is used as the organic solvent, separation by distilling off the organic solvent is preferable, and in a case where toluene is used as the organic solvent, the liquid-liquid separation is preferable. In a case where liquid-liquid separation has been carried out, distillation (concentration) may be carried out thereafter in consideration of the solubility of the target product.

Neutralization crystallization may be carried out by a conventional method and can be carried out by gradually adding an acid to the target liquid containing orotic acid and an orotic acid derivative to lower the pH. The acid used for neutralization crystallization is not particularly limited; however, an inorganic acid is preferable. Examples of the inorganic acid include hydrochloric acid, sulfuric acid, and nitric acid, and hydrochloric acid is preferable.

Neutralization crystallization is preferably carried out until the pH of the liquid phase reaches about a pH of 4 to 6, more preferably carried out until the pH reaches about 4.5 to 6, and still more preferably carried out until the pH reaches about 4.5 to 5.5. In a case where the pH is lower than 4, even the orotic acid derivative may also be precipitated.

The temperature at which neutralization crystallization is performed is not particularly limited; however, it can be, for example, in the range of 15° C. to 50° C. In a case where the temperature at which neutralization crystallization is performed is equal to or more than the above lower limit value, impurities are less likely to precipitate, and in a case where the temperature is equal to or less than the above upper limit value, the decrease of the recovery rate can be prevented.

By this step, orotic acid can be selectively precipitated from a liquid composition in which orotic acid and an orotic acid derivative are mixed. The precipitated orotic acid crystals can be removed by filtration or the like. In this manner, the precipitated orotic acid crystals and the liquid containing the orotic acid derivative can be separated. For filtration, a commercially available filtration filter or the like can be used. In this manner, the purity of the orotic acid derivative in the filtrate can be improved without performing column chromatography or the like. As a result, a liquid containing an orotic acid derivative with high purity can be obtained.

[Other Steps]

The production method of the present embodiment may include other steps in addition to the condensation step and the neutralization crystallization step. Examples of the other steps include a secondary neutralization crystallization step of precipitating crystals of an orotic acid derivative by neutralization crystallization, a crystal collection step of collecting crystals of an orotic acid derivative, and an orotic acid halogenation step of synthesizing an orotic acid halide.

(Secondary Neutralization Crystallization Step)

The secondary neutralization crystallization step is a step of subjecting the liquid containing the orotic acid derivative obtained in the neutralization crystallization step to neutralization crystallization to precipitate crystals of the orotic acid derivative.

The neutralization crystallization in this step may also be carried out by a conventional method, and an inorganic acid is preferably used. Examples of the inorganic acid include hydrochloric acid, sulfuric acid, and nitric acid, and hydrochloric acid is preferable.

The neutralization crystallization in this step is preferably carried out until the pH of the liquid phase reaches about 0.5 to 2, more preferably carried out until the pH reaches about 0.5 to 1.5, and still more preferably carried out until the pH reaches about 0.8 to 1.2.

By this step, the orotic acid derivative can be selectively precipitated from the liquid containing the orotic acid derivative. The obtained orotic acid derivative is obtained as a salt of the acid used for acidifying the liquid. The salt of the orotic acid derivative can be converted to a free orotic acid derivative by neutralizing with an equivalent amount of a basic compound. As the basic compound, sodium hydroxide, potassium hydroxide, calcium hydroxide, sodium phosphate salt, potassium phosphate salt, ammonia, or the like can be used.

(Crystal Collection Step)

The crystal collection step is a step of collecting crystals of the orotic acid derivative after the secondary neutralization crystallization step.

The crystals of the orotic acid derivative can be collected, for example, by filtration or the like. For filtration, a commercially available filtration filter or the like can be used.

(Orotic Acid Halogenation Step)

The orotic acid halogenation step is a step of halogenating orotic acid to obtain an orotic acid halide represented by General Formula (I), which is a raw material for the condensation reaction. The halogenation of orotic acid can be performed by a known method. For example, an orotic acid halide can be obtained by reacting orotic acid with an electrophilic halogenating agent such as thionyl halide ($SOX_2$; X is a halogen atom). This step is preferably carried out in the presence of a catalytic amount of N,N-dimethylformamide by dissolving orotic acid in a solvent such as toluene. The reaction temperature can be, for example, 50° C. to 90° C. It is preferable to use a glass lining reactor for the reaction. Since a metal container liquates out, the metal container is not suitable as a reaction container for this reaction.

In the halogenation reaction of orotic acid, the concentration of orotic acid in the reaction solution at the start of the reaction is preferably 5% to 20% by mass and more preferably 10% to 15% by mass. In a case where the concentration of orotic acid is equal to or more than the above lower limit value, the industrial productivity is good, and in a case where the concentration of the orotic acid halide is equal to or less than the above upper limit value, it is possible to prevent a decrease in yield due to the progression of side reactions.

The halogenation reaction of orotic acid may be carried out in air or may be carried out in a nitrogen gas atmosphere. The reaction is preferably carried out in the air.

The reaction for generating an orotic acid halide (3) from an orotic acid (1) and a thionyl halide (2) is shown below. In the following formula, X represents a halogen atom.

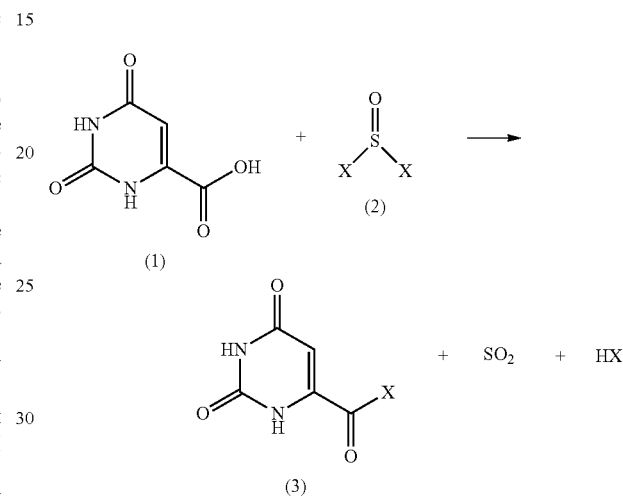

In addition to the above steps, the production method of the present embodiment may include, without particular limitation, a step commonly used as a method for purifying a chemical substance, such as a washing step or a drying step under reduced pressure.

According to the production method of the present embodiment, orotic acid and the orotic acid derivative can be separated by a simple method without performing column chromatography or the like. As a result, a highly purified orotic acid derivative can be obtained. Further, the production method of the present embodiment can be carried out using relatively inexpensive reagents.

As a result, the production method of the present embodiment is useful as a method for industrially producing an orotic acid derivative at a low cost.

EXAMPLES

The present invention will be described with reference to Examples, but the present invention is not limited to Examples below.

[Analysis Method]

Analysis by high-performance liquid chromatography (HPLC) was used to study the synthesis of orotic acid derivatives. The HPLC conditions used in the analysis are shown below.

<HPLC Analysis Conditions>

Column: Shodex (registered trade mark) RSpak NN814 (manufactured by Showa Denko K.K.)×2

Column temperature: 40° C.

Eluent: an aqueous solution adjusted to contain 0.1 w/v % phosphoric acid and 8 mM monopotassium dihydrogen phosphate as the concentration in the liquid.

Eluent flow rate: 1.5 mL/min
Sample injection volume: 20 μL
Detector: UV detector (230 nm)
<Synthesis of Orotic Acid Chloride>

Synthesis Example 1

Orotic acid (7.8 g, Thermo Fisher Scientific, Inc.), toluene (34 g, Junsei Chemical Co., Ltd.), and N,N-dimethylformamide (DMF, 1.0 g, Junsei Chemical Co., Ltd.) were added to a four-necked flask equipped with a Dimroth condenser tube, a Teflon (registered trade mark) stirring blade, a funnel for dropwise addition, and a thermometer, and stirred for several minutes. Then, thionyl chloride ($SOCl_2$, 8.9 g, 1.5 equivalents to the mole number of orotic acid, Tokyo Chemical Industry Co., Ltd.) was added thereto over 10 minutes using the funnel for dropwise addition. The four-necked flask was immersed in an oil bath and maintained at about 80° C. while stirring. Five hours after the temperature reached about 80° C., 200 μL of the reaction solution in the four-necked flask was sampled. The sampled reaction solution was added to 3 mL of dehydrated methanol, stirred lightly, and then left to stand for about 10 minutes. Then, the orotic acid methyl ester in the sampled reaction solution was analyzed by HPLC. The yield of orotic acid chloride based on the orotic acid calculated from the analysis value of the orotic acid methyl ester was 93%.

Next, the reaction solution in the four-necked flask was cooled to room temperature (about 25° C.) and filtered using a Kiriyama funnel (registered trade mark) to obtain crystals precipitated in the reaction solution. The crystals obtained on the filter paper were washed with 8 times their weight of toluene and then dried at room temperature at about 3 kPa for about 1 hour to remove the solvent. The amount of orotic acid chloride obtained was 7.2 g.

<Condensation Reaction>

Example 1

<<Condensation Reaction Between Orotic Acid Chloride and Glutamic Acid Using Water as Reaction Solvent>>

Ion-exchanged water (100 g), sodium glutamate monohydrate (3.4 g, 2 equivalents to orotic acid chloride), and a 48% aqueous sodium hydroxide solution (3.4 g, 4 equivalents to orotic acid chloride) were added to a 200-mL four-necked flask equipped with a Teflon (registered trade mark) stirring blade and a thermometer. Orotic acid chloride (1.8 g) synthesized by the same method as in Synthesis Example 1 and the 48% aqueous sodium hydroxide solution (1.9 g) were each divided into 5 aliquots and added alternately to the four-necked flask which had been ice-cooled so that the liquid temperature was maintained at 5° C. or lower. After the addition, the reaction solution was stirred at 5° C. or lower for 1 hour. The pH of the reaction solution was 11.3. A part of this reaction solution was sampled, and N-orotinyl glutamic acid in the sampled reaction solution was analyzed by HPLC. The yield of N-orotinyl glutamic acid based on the orotic acid chloride calculated from the analysis value was 79%.

Example 2

<<Condensation Reaction Between Orotic Acid Chloride and Glutamic Acid in Mixed System of Organic Solvent and Water>>

A solution (200 g) obtained by mixing toluene with ion-exchanged water at a mass ratio of 2:1, sodium glutamate monohydrate (4.1 g, 1.2 equivalents to orotic acid chloride), and a 48% aqueous sodium hydroxide solution (4.1 g, 2.4 equivalents to orotic acid chloride) were added to a 300-mL four-necked flask equipped with a Teflon (registered trade mark) stirring blade, a pH meter, and a thermometer. Orotic acid chloride (3.6 g) synthesized by the same method as in Synthesis Example 1 was added little-by-little to the four-necked flask which had been ice-cooled so that the liquid temperature was maintained at 5° C. or lower. During the addition and reaction of orotic acid chloride, the pH of the reaction solution (in the suspended state) was monitored with a pH meter, and a 48% aqueous sodium hydroxide solution was automatically supplied by a supply pump so that the pH was maintained at 11.6. The amount of the 48% aqueous sodium hydroxide solution supplied to the reaction solution by the completion of the reaction was 4.0 g. After the addition of orotic acid chloride, the reaction solution was stirred at 5° C. or lower for 1 hour. Then, a part of the reaction solution was sampled, and N-orotinyl glutamic acid in the sampled reaction solution was analyzed by HPLC. The yield of N-orotinyl glutamic acid based on the orotic acid chloride calculated from the analysis value was 75%.

After completion of the reaction, the reaction solution was transferred to a separating funnel and separated into an organic layer containing toluene and an aqueous layer.

Example 3

<<Condensation Reaction Between Orotic Acid Chloride and Glutamic Acid in Mixed System of Organic Solvent and Water>>

A solution (200 g) obtained by mixing tetrahydrofuran with ion-exchanged water at a mass ratio of 2:1, sodium glutamate monohydrate (4.1 g, 1.2 equivalents to orotic acid chloride), and a 48% aqueous sodium hydroxide solution (4.1 g, 2.4 equivalents to orotic acid chloride) were added to a 300-mL four-necked flask equipped with a Teflon (registered trade mark) stirring blade, a pH meter, and a thermometer. Orotic acid chloride (3.6 g) synthesized by the same method as in Synthesis Example 1 was added little-by-little to the four-necked flask which had been ice-cooled so that the liquid temperature was maintained at 5° C. or lower. During the addition and reaction of orotic acid chloride, the pH of the reaction solution was monitored with a pH meter, and a 48% aqueous sodium hydroxide solution was automatically supplied by a supply pump so that the pH was maintained at 11.9. The amount of the 48% aqueous sodium hydroxide solution supplied to the reaction solution by the completion of the reaction was 4.2 g. After the addition of orotic acid chloride, the reaction solution was stirred at 5° C. or lower for 1 hour. Then, a part of the reaction solution was sampled, and N-orotinyl glutamic acid in the sampled reaction solution was analyzed by HPLC. The yield of N-orotinyl glutamic acid based on the orotic acid chloride calculated from the analysis values was 89%.

<Crystallization>

Example 4

36% hydrochloric acid was added to 55 g of an aqueous layer containing 2.0 g of N-orotinyl glutamic acid synthesized by the same method as in Example 2 and containing 0.4 g of orotic acid to adjust the pH to 5. Crystals of orotic acid precipitated due to a change in pH were removed by filtration to obtain a filtrate. Crystals of N-orotinyl glutamic acid hydrochloride were precipitated by adding 36% hydrochloric acid to the obtained filtrate to adjust the pH to 1. The crystals in this liquid were obtained by filtration and washed with about 10 g of cold water.

The recovery rate of orotinyl glutamic acid recovered by this operation was 33%, and the removal rate of orotic acid was 99%. The ratio (the mass ratio) of orotic acid to orotinyl glutamic acid hydrochloride in the obtained crystals was 0.7%.

Comparative Example 1

106 g of an aqueous layer containing 2.0 g of N-orotinyl glutamic acid synthesized in the same manner as in Example 2 and 0.35 of orotic acid were filtered through a filter to obtain a filtrate. The obtained filtrate was concentrated under reduced pressure until the amount was to be 20 g, and crystals were precipitated. The crystals in this liquid were obtained by filtration and washed with about 10 g of cold water.

The orotinyl glutamic acid recovered by this operation was in hydrochloride form. The recovery rate was 58% and the removal rate of orotic acid was 68%. The ratio (the mass ratio) of orotic acid to orotinyl glutamic acid hydrochloride in the obtained crystals was 8.6%.

Comparative Example 2

N-orotinyl glutamic acid was synthesized by the same method as in Example 2, and crystals of N-orotinyl glutamic acid hydrochloride recovered by the same method as in Example 4 were used to prepare an aqueous solution containing 5 w/w % of N-orotinyl glutamic acid. Each of ethanol, methanol, isopropanol, acetone, and THF was added to 100 g of the solution to carry out anti-solvent crystallization. Regardless of which solvent was used for anti-solvent crystallization, the solution became jelly-like, and it was difficult to separate the crystals of orotinyl glutamic acid.

Comparative Example 3

N-Orotinyl glutamic acid was synthesized by the same method as in Example 2, and crystals of N-orotinyl glutamic acid hydrochloride recovered by the same method as in Example 4 were used to prepare a slurry solution (dispersion medium:water) containing 10 w/w % of orotinyl glutamic acid. 100 g of the slurry liquid was heated to 80° C. to dissolve crystals of N-orotinyl glutamic acid. The solution was cooled gradually. With cooling, the liquid property became jelly-like, and it was difficult to separate the crystals of orotinyl glutamic acid.

INDUSTRIAL APPLICABILITY

The present invention provides an inexpensive and industrially feasible method for producing an orotic acid derivative.

What is claimed is:

1. A method for producing an orotic acid derivative, comprising:
performing, under a basic condition, a condensation reaction between an orotic acid halide represented by General Formula (I) and a compound represented by General Formula (II) to generate an orotic acid derivative represented by General Formula (III); and
precipitating crystals of orotic acid by neutralization crystallization to separate a liquid containing the orotic acid derivative from the crystals of orotic acid, after the condensation reaction,

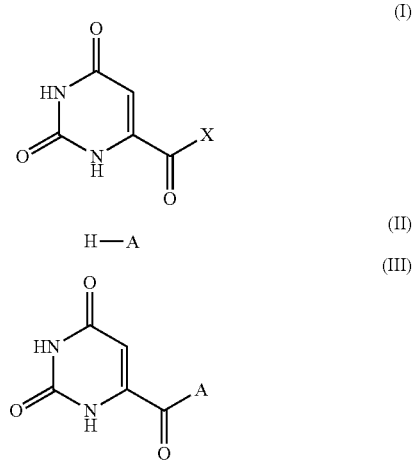

wherein X is a halogen atom, and A is a group represented by General Formula (A-1) or (A-2);

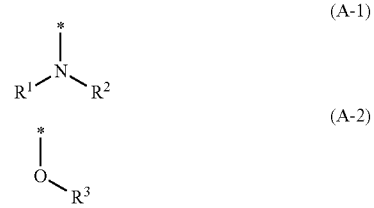

wherein $R^1$ is a hydrogen atom or an organic group, and $R^2$ and $R^3$ are each independently an organic group, in a case where $R^1$ is an organic group, $R^1$ and $R^2$ may be bonded to each other to form a ring, and * is a bonding position at which the hydrogen atom in General Formula (II) is bonded.

2. The method for producing an orotic acid derivative according to claim 1, wherein in General Formula (A-1), le is a hydrogen atom or an organic group having 1 to 10 carbon atoms, and $R^2$ is an organic group having a carboxy group and having 1 to 15 carbon atoms, and
in General Formula (A-2), $R^3$ is an organic group having 1 to 15 carbon atoms.

3. The method for producing an orotic acid derivative according to claim 1, wherein the compound represented by General Formula (II) is an amino acid.

4. The method for producing an orotic acid derivative according to claim 3, wherein the amino acid is glutamic acid.

5. The method for producing an orotic acid derivative according to claim 1, to wherein a solvent used in the condensation reaction is a non-halogenic solvent.

6. The method for producing an orotic acid derivative according to claim 5, wherein the solvent is a water-containing solvent.

7. The method for producing an orotic acid derivative according to claim 6, wherein the solvent is a two-phase solvent of an organic solvent and water.

8. The method for producing an orotic acid derivative according to claim 7, wherein the organic solvent is tetrahydrofuran or toluene.

9. The method for producing an orotic acid derivative according to claim 1, wherein a pH of a liquid phase is set to 4 to 6 in the neutralization crystallization step.

10. The method for producing an orotic acid derivative according to claim 1, further comprising subjecting the liquid containing the orotic acid derivative to secondary neutralization crystallization to precipitate crystals of the orotic acid derivative, after the neutralization crystallization.

11. The method for producing an orotic acid derivative according to claim 10, wherein a pH of a liquid phase is set to 0.5 to 2 in the secondary neutralization crystallization.

12. The method for producing an orotic acid derivative according to claim 10, further comprising collecting the crystals of the orotic acid derivative, after the secondary neutralization crystallization.

13. The method for producing an orotic acid derivative according to claim 1, further comprising reacting an orotic acid with a thionyl halide to generate the orotic acid halide, before the condensation reaction.

14. The method for producing an orotic acid derivative according to claim 1, wherein the orotic acid halide is orotic acid chloride.

* * * * *